United States Patent [19]
Dobbs et al.

[11] Patent Number: 5,757,878
[45] Date of Patent: May 26, 1998

[54] DETECTOR ARRANGEMENT FOR X-RAY TOMOGRAPHY SYSTEM

[75] Inventors: John Dobbs, Hamilton; Ruvin Deych, Burlington, both of Mass.

[73] Assignee: Analogic Corporation, Peabody, Mass.

[21] Appl. No.: 698,717

[22] Filed: Aug. 16, 1996

[51] Int. Cl.$^6$ ........................................... A61B 6/03
[52] U.S. Cl. ................................... 378/19; 378/4
[58] Field of Search ............................ 378/19, 4, 7

[56] References Cited

U.S. PATENT DOCUMENTS

| | | | |
|---|---|---|---|
| 4,338,521 | 7/1982 | Shaw et al. | 250/366 |
| 4,417,354 | 11/1983 | Pfeiler | 378/19 |
| 5,025,462 | 6/1991 | Saito et al. | 378/19 |
| 5,463,224 | 10/1995 | Burstein et al. | 250/366 |
| 5,487,098 | 1/1996 | Dobbs et al. | 378/19 |

*Primary Examiner*—David P. Porta
*Attorney, Agent, or Firm*—Lappin & Kusmer LLP

[57] ABSTRACT

In an x-ray scanning system having an x-ray source and a plurality of x-ray detectors mounted in substantially linear arrays and positioned along an arc extending about a focal spot defined by the x-ray source, the placement of the arrays along the arc is optimized to substantially avoid interfering contact between adjacent arrays. Each detector array is located at a preselected radial distance from the focal spot and oriented at a preselected angle with respect to radial lines extending from the focal spot so that the radiation-insensitive end portions of adjacent arrays overlap in the tangential direction. The tangential spacing between adjacent detector arrays is thus approximately equal to the tangential spacing between adjacent detectors in a single array.

6 Claims, 4 Drawing Sheets

DETECTOR ARRANGEMENT FOR X-RAY TOMOGRAPHY SYSTEM

TECHNICAL FIELD

This invention relates generally to x-ray computed tomography (CT) systems, and more particularly to arrangements for x-ray detector assemblies within such systems.

BACKGROUND OF THE INVENTION

Third-generation CT scanners typically include an x-ray source and an array of x-ray detectors secured respectively on diametrically opposite sides of an annular disk, the latter being rotatably mounted within a gantry support. During a scan of a patient located within the opening of the disk, the disk rotates about a rotation axis while x-rays pass from the focal spot of the x-ray source through the patient to the detector system.

The x-ray source and detector array are positioned so that the x-ray paths between the focal spot and each detector all lie in the same plane (the so-called "slice plane", "rotation plane" or "scanning plane") which is normal to the rotation axis of the disk. Because the ray paths originate from substantially a point source and extend at different angles to the detectors, the ray paths resemble a fan, and thus the term "fan beam" is used to describe all of the ray paths at any one instant of time. The radiation that is detected by a single detector at a measuring instant during a scan is considered a "ray" or "beam". The ray is partially attenuated by the mass of the patient in its path, and each detector generates a single intensity measurement as a function of the integral of the attenuation, and thus of the density of the portion of the patient in the path of the ray from the focal spot to that detector. These x-ray intensity measurements, or projections, are typically performed during prescribed measurement intervals at each of a plurality of angular disk positions.

Various types of detectors have been developed, including gas and solid state types. A typical solid state detector (hereinafter, "detector" or "detector channel") includes a scintillating crystal which converts high energy x-radiation photons into low energy visible light photons, and a photodiode which converts the low energy visible light photons into extremely low-amplitude electrical currents (i.e., on the order of picoamperes to nanoamperes). The output of each detector represents the x-ray flux incident on the detector crystal. The outputs of the detectors are transmitted via an array of conductors to a data acquisition system (DAS) for signal processing.

Because the resolution of the resulting image is a function of the size of the detectors, a CT scanner system typically includes hundreds of detectors which are extremely closely spaced along an arc extending about the focal spot. For reducing the costs of such detector arrays, the use of preassembled solid state detector modules, each comprising several solid state detectors, has been described in U.S. Pat. No. 5,487,098 issued to John Dobbs and David Banks, and assigned to the present assignee. For example, one third-generation CT scanner system manufactured by the present assignee includes 384 detectors provided by 24 modules of 16 detectors each and closely spaced along an arc which subtends not more than 48 degrees. The width of a single detector is thus on the order of a millimeter.

Each detector in a module is typically surrounded on five sides by a highly reflective material. This material is substantially transparent to x-rays, yet it prevents excessive light leakage between crystals, thus substantially reducing or eliminating optical cross-talk between adjacent detector channels. In addition, the reflective material reflects visible light generated by a crystal onto the underlying photodiode, thereby increasing the signal level from that crystal.

The highly reflective material between the detector crystals effectively separates them from one another by approximately 0.2 millimeter. For convenience in handling and in manufacturing, the detectors are typically grouped in generally linear arrays of at least 16 detectors per array. Because the detectors must be closely spaced along a generally arcuate curve extending about the focal spot, the construction of generally linear arrays of multiple detectors makes it extremely difficult to place the detectors uniformly along the arcuate path. Moreover, the dimensions of the individual arrays vary somewhat due to normal manufacturing tolerances, and thus the spacing between the detector arrays must be sufficient to accommodate such variations.

The regions of reflective material between individual detector channels of a single array define a uniform spacing of detectors within that array. It would be an advantage in the art of x-ray scanning systems to maintain the uniformity of this inter-detector spacing within and throughout the entire detector assembly, which typically comprises several generally linear arrays.

OBJECTS OF THE INVENTION

It is therefore an object of the present invention to provide an x-ray scanning system in which the placement of substantially linear arrays of detectors along a generally arcuate path extending about the focal spot can be optimized to avoid mechanical interference between adjacent detector arrays.

It is another object of the invention to provide an x-ray scanning system in which the tangential spacing and positioning of the detector arrays can be optimized by varying the radial spacing and positioning of the detector arrays.

SUMMARY OF THE INVENTION

The detector channels of the present invention receive x-rays emanating in straight lines directly from the focal spot of the x-ray source. Because the x-rays travel radially outward from this point, it is desirable to have uniformly spaced detectors in order to ensure uniform radiation detection. In addition, because the detectors are constructed in generally linear arrays which are positioned along a generally arcuate or curved path, it is desirable to position the arrays to achieve a substantially uniform spacing without interference between the arrays.

In the present invention, this problem is addressed by staggering the detector arrays radially in order to overlap the radiation-insensitive portions of adjacent arrays in the tangential direction. By overlapping these portions of adjacent arrays, it is not necessary to provide additional tangential spacing between each array to accommodate variations in the dimensions of the arrays, particularly in the tangential direction.

An x-ray scanning system according to the invention includes (a) a gantry including a disk for supporting at least an x-ray source, and a frame for rotatably supporting the disk for rotation about a rotation axis, (b) an x-ray detector assembly including a plurality of x-ray detectors cooperative with the x-ray source, (c) a support structure connected to the disk for supporting the detector assembly, and (d) a data acquisition system for processing signals received from the detectors. The x-ray source defines a focal spot from which x-rays are emitted. The detectors are grouped in a plurality of substantially linear arrays which are located along an arc extending about the focal spot. According to the invention, the x-ray scanning system includes means for optimizing the placement of the arrays along the arc to substantially avoid interfering contact of adjacent arrays. The radial distances of respective detector arrays from the focal spot are varied so that portions of the ends of adjacent arrays overlap in the tangential direction. The tangential spacing between adjacent arrays is thus made approximately equal to the tangential spacing between adjacent detectors in a single array.

In one embodiment, the detector arrays are positioned to be substantially perpendicular to radial lines extending from the focal spot and are radially staggered in a regular crenelated pattern, in which adjacent detector arrays are located at different radial distances from the focal spot.

In an alternate embodiment, the detector arrays are all tilted at a preselected angle α with respect to radial lines extending from the focal spot. The arrays are staggered in a "fishscale" pattern, in which all the detector arrays are located at substantially the same radial distance from the focal spot.

The x-ray scanning system of the invention can further include an anti-scatter plate assembly mounted on the support structure and including a plurality of anti-scatter plates disposed between the x-ray source and the detector assembly. The anti-scatter plates are preferably positioned to be substantially aligned with radial lines extending from the focal spot.

These and other objects and advantages of the invention will in part be obvious and will in part appear hereinafter. The invention accordingly comprises the apparatus possessing the construction, combination of elements and arrangement of parts which are exemplified in the following detailed disclosure, the scope of which will be indicated in the claims.

BRIEF DESCRIPTION OF THE DRAWINGS

For a fuller understanding of the nature and objects of the present invention, reference should be had to the following detailed description taken in connection with the accompanying drawings, in which.

DETAILED DESCRIPTION OF THE DRAWINGS

The term "radial", as used herein, refers to a direction from or toward the focal spot of the x-ray source within the scanning plane, i.e., within a plane perpendicular to the axis of rotation of the scanner. The term "tangential", as used herein, refers to a direction within the scanning plane which is substantially perpendicular to the radial direction.

The CT scanner system of the present invention substantially eliminates the need to provide tangential spacing between detector arrays which is greater than the distance between adjacent detectors within a single array. To accommodate variations in the dimensions of the detector arrays in the tangential direction, adjacent detector arrays are staggered radially so that the ends of adjacent detector arrays, and more particularly the radiation-insensitive portions at the ends of adjacent arrays, overlap in the tangential direction. The overlap of these portions of the detector arrays in the tangential direction provides optimal and uniform spacing of the arrays along the arcuate edge of the fan-shaped radiation beam.

In one embodiment, the detector arrays are uniformly tilted at a preselected angle α with respect to radial lines extending from the focal spot, and all the arrays are located at substantially the same radial distance from the focal spot. In an alternate embodiment, the detector arrays are oriented substantially perpendicular to radial lines extending from the focal spot, yet they are staggered radially, i.e., adjacent detector arrays are placed at different radial distances from the focal spot.

By overlapping the edge regions of adjacent detector arrays, the tangential spacing between adjacent arrays can be made approximately equal to the tangential spacing (defined by the region of reflective material) between adjacent detector channels within a single array. This positioning of the detector arrays effectively eliminates the need for additional tangential space to accommodate normal variations in the as-manufactured dimensions of the arrays.

Figure 1:
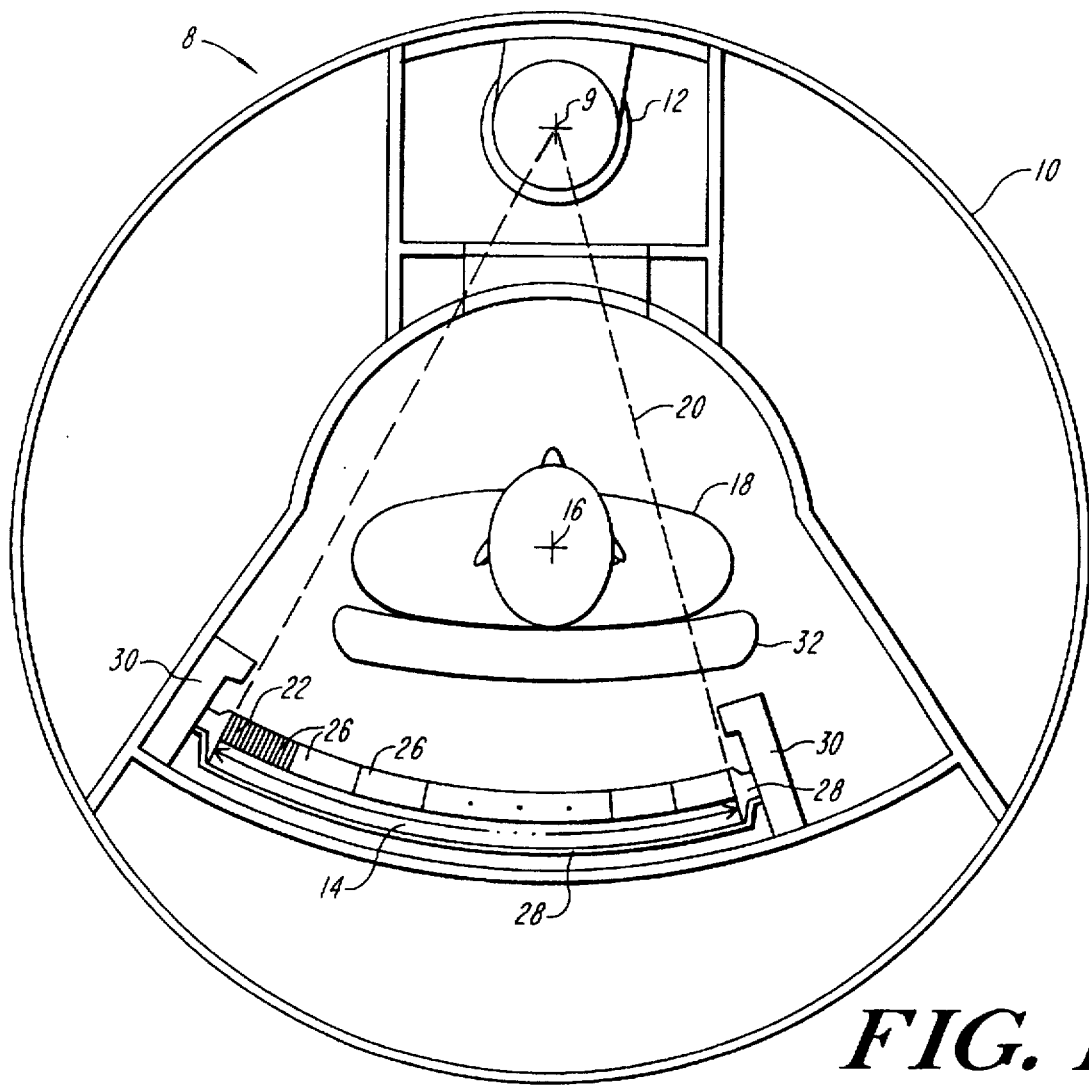
FIG. 1 is an axial view of a CT scanner system according to the present invention.

FIG. 1 represents a CT scanner system according to the present invention. To provide the data for a CT scan, scanner 8 includes a source 12 of X-rays and a detector assembly 14 mounted to a disk 10. Source 12 and detector assembly 14 are rotated about a rotation axis 16 (extending normal to the view shown in FIG. 1) so as to rotate around the object 18 that extends through the central opening of the disk during the CT scan. Object 18 may be a part of a live human patient, such as the head or torso. Source 12 emits within the scanning plane (normal to rotation axis 16) a continuous fan-shaped beam 20 of X-rays, which emanates from a focal spot 9 and extends to and is sensed by the detectors of assembly 14 after passing through object 18. An array of anti-scatter plates 22 is located between object 18 and the detectors of assembly 14 to substantially reduce the amount of scattered radiation sensed by the detectors.

In the preferred embodiment the detectors number 384 and cover an arc of 48°, although the number and angle can vary. Referring again to FIG. 1, disk 10, which may advantageously be of a lightweight material, such as aluminum, is caused to rotate rapidly and smoothly around axis 16. The disk 10 is of an open frame construction so that object 18 can be positioned through the opening of the disk. Object 18 may be supported, for example, on a pallet or table 32, which should be as transparent as practical to x-rays. As disk 10 rotates, detectors of assembly 14 are periodically sampled to provide discrete measurements of x-rays passing in the scanning plane through object 18 from many projection angles. The measurements are then processed electronically with appropriate signal processing equipment (not shown), in accordance with well-known mathematical techniques, so as to produce the final image information. The image information may then be placed in memory, analyzed in a computer, or suitably displayed.

The detector assembly 14 includes a base support element in the form of a supporting spine 28. The detectors and anti-scatter plates are each assembled into a plurality of identical respective modules 24 and 26. The modules are then accurately aligned and secured to the spine 28, and the spine supported by disk 10 with suitable supports, such as supports 30, so that the detectors all lie in the scanning plane and subtend an equal angle with respect to the focal spot 9 of the x-ray source 12.

Figure 2:
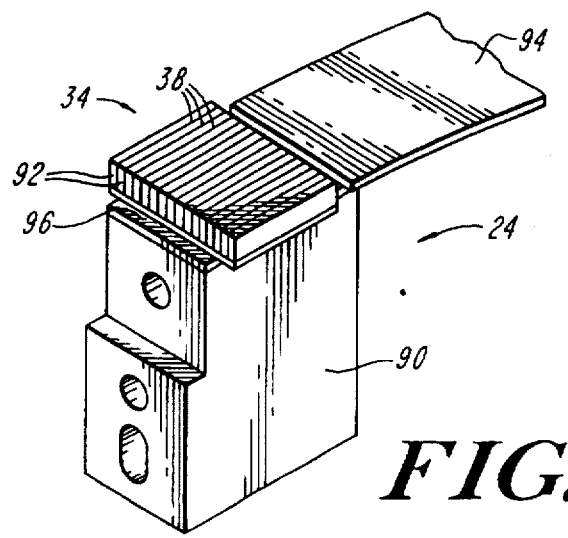
FIG. 2 is a perspective view of a preferred embodiment of a detector module according to the present invention.

A preferred form of the detector module 24 is shown in detail in FIG. 2. This module comprises a metal block 90 with a substantially linear array 34 of solid state detectors 92 and a multi-conductor ribbon cable 94, or other flexible connector, mounted on one face 96 thereof. A photodiode 97 underlies the array 34 and converts x-ray photons into visible light photons.

At least a portion of block 90 is preferably narrower than the array 34, to facilitate close placement of the detector arrays without interference of the blocks 90 with one another or with an array 34. In the illustrated embodiment, the width of the block 90 is uniformly less than the width of the array 34; however, other configurations which facilitate placement of the arrays to avoid interference between adjacent blocks and/or arrays are within the scope of the present invention.

Figure 3:
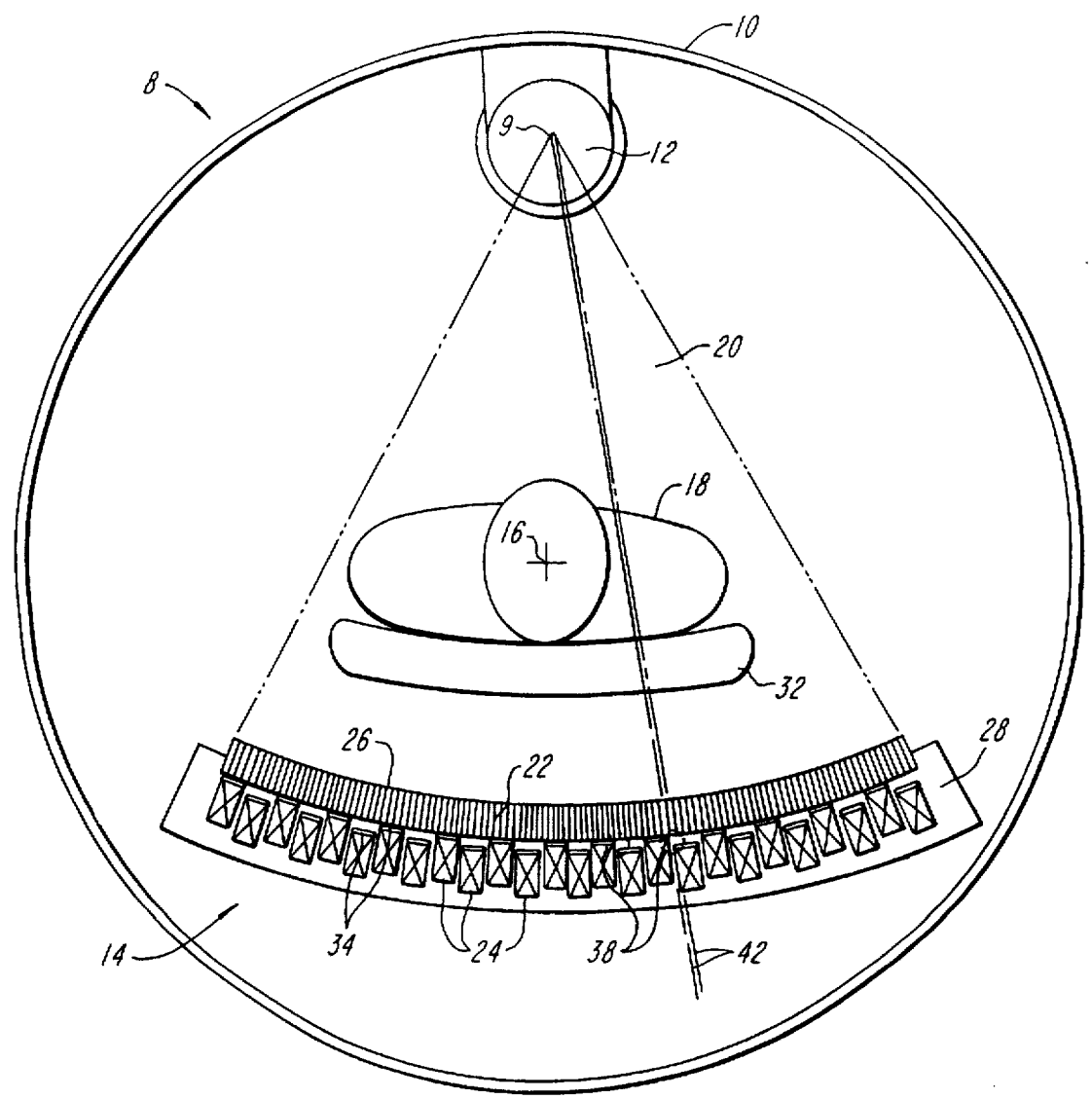
FIG. 3 is a simplified axial view of a portion of a CT scanner system according to one embodiment of the invention.
Figure 4:
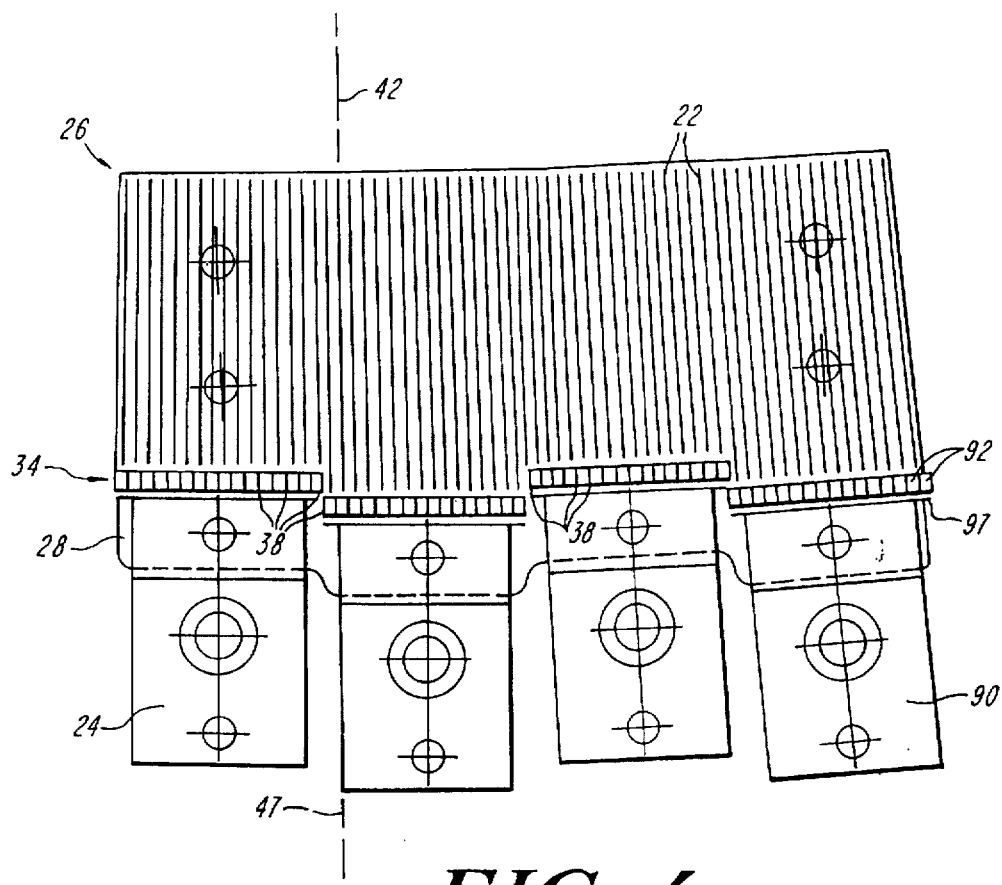
FIG. 4 is a detail plan view of the modular detector and anti-scatter plate assemblies as mounted on the support structure according to the embodiment of FIG. 3.

A CT scanner system employing one embodiment of the detector module arrangement of the present invention is illustrated in FIGS. 3 and 4. According to this embodiment, sixteen detector crystals 92 are mounted in a substantially linear array 34 on a modular block 90. As shown more clearly in FIG. 4, the array 34 extends beyond the edges of the block 90 so that adjacent detector arrays can be closely spaced along an arc extending about the focal spot without mutual interference. Although each detector array is substantially perpendicular to radial lines 42 extending from the focal spot 9, adjacent detector arrays are positioned to be at different radial distances from the focal spot. Portions of adjacent detector arrays 34 comprising the radiation-insensitive regions of reflective material 38 at the ends of the arrays overlap in the tangential direction so that the tangential spacing between adjacent arrays is approximately equal to the tangential spacing between adjacent detector crystals (i.e., the thickness of the region of reflective material between crystals) of a single array.

To preclude the impingement of stray or scattered radiation on the detector crystals, particularly from the irradiation of dense matter, an array of elongated, thin "anti-scatter" plates 22 is positioned between the x-ray source and the detectors. The anti-scatter plates are opaque to x-rays and are aligned relative to the detectors so as to permit passage of substantially only those rays traversing a straight line from the source to a detector. The anti-scatter plates are generally placed so that they are aligned along radial lines 42 extending from the focal spot and block any rays that impinge on the detector crystal at an angle which varies, for example, by more than about three degrees from a normally incident ray along the respective ray path.

FIG. 4 is a detail view of a portion of the CT scanner system according to the embodiment of FIG. 3, in which two pairs of detector modules 24 and a single anti-scatter plate module 26 are mounted on a support structure or spine 28. Adjacent detector modules 24 are positioned at different radial distances from the focal spot (not shown), with end portions 38 of the adjacent arrays overlapping in the tangential direction.

Figure 6:
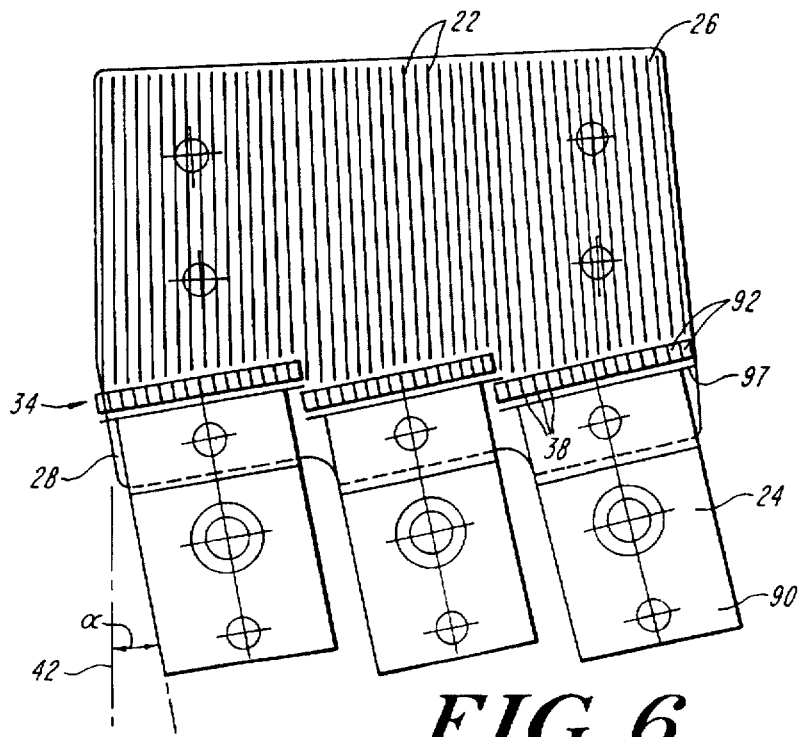
FIG. 6 is a detail plan view of the modular detector and anti-scatter plate assemblies on the support structure according to the embodiment of FIG. 5.
Figure 5:
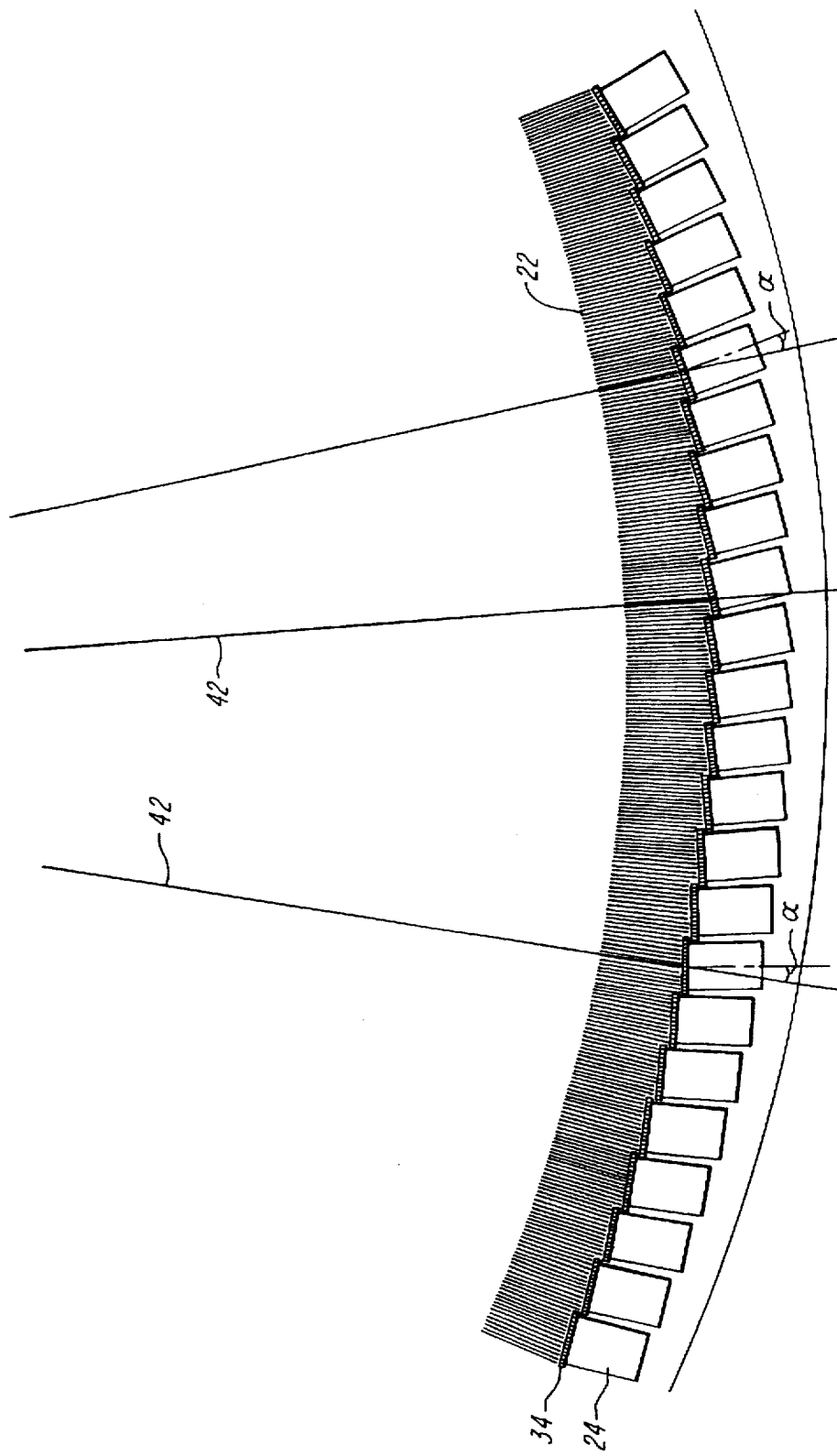
FIG. 5 is an axial view of a CT scanner system according to an alternate embodiment of the invention.

A CT scanner system employing an alternate embodiment of the detector module arrangement of the present invention is illustrated in FIGS. 5 and 6. According to this embodiment, sixteen detector crystals 92 are mounted in a substantially linear array 34 on a modular block 90. As shown more clearly in FIG. 6, the array 34 extends beyond the edges of the block 90 so that the detector arrays can be closely spaced along the fan beam arc without mutual interference. Each of the detector modules 24 is tilted by a preselected angle α relative to radial lines 42 extending from the focal spot 9 (not shown). According to this embodiment, adjacent detector modules are positioned at substantially the same radial distance from the focal spot, yet tilted at a preselected angle α from a nominally perpendicular orientation to obtain a tangentially overlapping, or "fish-scale", pattern of detector modules. For this embodiment, the angle α is selected to permit the radiation-insensitive end portions 38 of adjacent detector arrays to overlap each other in the tangential direction sufficiently so that, as in the embodiment of FIGS. 3 and 4, the tangential spacing between adjacent detector arrays is approximately equal to the thickness of the region of reflective material between adjacent detector crystals of a single array. In a preferred embodiment the angle α can vary between, for example, about 7 and 11 degrees. The angle may be uniform for all the detector arrays, or it may vary depending on the location of the array. This so-called "fishscale" pattern is a variation of the staggered pattern illustrated in FIGS. 3 and 4 and achieves a similar result. Other radially staggered array patterns which permit optimum spacing of the arrays within the detecting zone are considered to be within the scope of the invention.

FIG. 6 is a detail view of a portion of the CT scanner system according to the embodiment of FIG. 5, in which three detector modules 24 and one anti-scatter plate module 26 are mounted on a support structure, or spine, 28. The anti-scatter plate module 26 is positioned and secured relative to the detector modules 24 so that the anti-scatter plates 22 are substantially aligned with radial lines 42 extending from the focal spot.

Because certain changes may be made in the above apparatus without departing from the scope of the invention herein disclosed, it is intended that all matter contained in the above description or shown in the accompanying drawings shall be interpreted in an illustrative and not a limiting sense.

What is claimed is:

1. An x-ray scanning system including (a) a gantry including a disk for supporting at least an x-ray source, and a frame for rotatably supporting the disk for rotation about a rotation axis, (b) an x-ray detector assembly including a plurality of x-ray detectors cooperative with said x-ray source, wherein said x-ray source defines a focal spot from which radiation is emitted, said detectors being grouped in a plurality of substantially linear arrays fixedly positioned substantially along an arc extending about the focal spot, (c) a support structure connected to said disk for supporting said detector assembly, and (d) a data acquisition system for processing signals received from said detectors, said x-ray scanning system further comprising:

means for optimizing the placement of, and securing, said detector arrays along said arc so that interfering contact of adjacent arrays is substantially avoided.

2. The x-ray scanning system of claim 1, wherein said means for optimizing the placement of said detector arrays comprises means for fixedly locating each array at: (a) a preselected angular orientation with respect to radial lines extending from the focal spot, and (b) a preselected radial distance from the focal spot, wherein portions of adjacent arrays overlap in the tangential direction so that the tangential spacing between adjacent detector arrays is approximately equal to the tangential spacing between adjacent detectors in a single array.

3. The x-ray scanning system of claim 2, wherein each of said detector arrays is fixedly positioned to be other than substantially perpendicular to radial lines extending from the focal spot, and wherein corresponding points of each of said arrays are located and secured at substantially the same radial distance from the focal spot.

4. The x-ray scanning system of claim 2 or 3, further comprising an anti-scatter plate assembly mounted on said support structure, said anti-scatter plate assembly including a plurality of anti-scatter plates disposed between the x-ray source and said detector assembly.

5. The x-ray scanning system of claim 4, wherein the anti-scatter plates are substantially aligned with radial lines extending from the focal spot.

6. The x-ray scanning system of claim 2, wherein each of said detector arrays is fixedly positioned to be substantially perpendicular to radial lines extending from the focal spot, and wherein adjacent detector arrays are located and secured at different radial distances from the focal spot.

* * * * *